US012746125B2

(12) United States Patent
Salomão et al.

(10) Patent No.: US 12,746,125 B2
(45) Date of Patent: Sep. 29, 2026

(54) TITANIUM MESH COVERED WITH BIOCOMPATIBLE POLYPROPYLENE FILM FOR COVERING AND PROTECTING BONE GRAFTS/BIOMATERIALS AND PROCESS FOR OBTAINING SAME

(71) Applicants: Munir Salomão, Sao Paulo (BR); Gabriela Meira Salomão Ambrizzi, Sao Paulo (BR)

(72) Inventors: Munir Salomão, Sao Paulo (BR); Gabriela Meira Salomão Ambrizzi, Sao Paulo (BR)

( * ) Notice: Subject to any disclaimer, the term of this patent is extended or adjusted under 35 U.S.C. 154(b) by 347 days.

(21) Appl. No.: 18/697,193

(22) PCT Filed: Jun. 22, 2023

(86) PCT No.: PCT/BR2023/050208
§ 371 (c)(1),
(2) Date: Mar. 29, 2024

(87) PCT Pub. No.: WO2024/000049
PCT Pub. Date: Jan. 4, 2024

(65) Prior Publication Data
US 2024/0398571 A1 Dec. 5, 2024

(30) Foreign Application Priority Data
Jun. 30, 2022 (BR) .......................... 1020220131236

(51) Int. Cl.
*A61F 2/28* (2006.01)
*A61F 2/30* (2006.01)
(Continued)

(52) U.S. Cl.
CPC .......... *A61F 2/2846* (2013.01); *A61L 27/306* (2013.01); *A61L 27/34* (2013.01);
(Continued)

(58) Field of Classification Search
CPC .......... A61F 2/2846; A61F 2002/30919; A61F 2/2875; A61F 2002/30971; A61F 2210/0076; A61L 27/365; A61L 2430/02
See application file for complete search history.

(56) References Cited

U.S. PATENT DOCUMENTS 5,380,328 A * 1/1995 Morgan .............. A61F 2/30965 606/70
2005/0288790 A1* 12/2005 Swords ................ A61F 2/2875 606/281
(Continued)

FOREIGN PATENT DOCUMENTS

BR 202013003809 U2 * 2/2017
CN 204364173 U * 6/2015

OTHER PUBLICATIONS

International Search Report, National Institute of Industrial Property (Brazil), Sep. 21, 2023.

*Primary Examiner* — Javier G Blanco
(74) *Attorney, Agent, or Firm* — Bay State IP, LLC

(57) ABSTRACT

The present invention pertains to the field of biomaterials for covering and protecting bone grafts/biomaterials, and relates more specifically to a titanium mesh covered with a biocompatible polypropylene film that aims to increase bone volume using biomaterials or using grafts in their most varied forms, such as autogenous bone (bone from the individual), allogenous bone (bone from other individuals of the same species), and xenogenous bone (bone from individuals of a different species) for the subsequent installation of osteointegrated implants. When the claimed mesh protected with a polypropylene film is used, with the film blocking the holes, the materials used to increase the volume do not pass through the holes of the mesh, as they are blocked by the polypropylene film, making these meshes 100% waterproof. This makes it easy to remove the mesh
(Continued)

and, as there is no penetration of material through the holes, the implants are installed over a large amount of bone tissue. When using the titanium mesh with the polypropylene film, in contrast to when it does not have this protection, it does not need to be completely covered by surgical flaps, facilitating the surgical technique and thus avoiding post-operative complications due to exposure that often occurs with unprotected meshes. In addition, it is advantageous that the mesh can be kept intentionally exposed to the mouth environment, placed over the materials used to achieve bone volume augmentation, regardless of the materials used underneath it, whether grafts or biomaterials (synthetic materials). This brings greater comfort to the patient, as it provides a post-operative period with very low morbidity and a rapid recovery.

1 Claim, 1 Drawing Sheet

(51) Int. Cl.
*A61L 27/30* (2006.01)
*A61L 27/34* (2006.01)
*A61L 27/36* (2006.01)
*A61L 27/56* (2006.01)

(52) U.S. Cl.
CPC ............ *A61L 27/365* (2013.01); *A61L 27/56* (2013.01); *A61F 2002/30321* (2013.01); *A61F 2002/30919* (2013.01); *A61F 2002/3092* (2013.01); *A61F 2310/00023* (2013.01); *A61L 2420/08* (2013.01); *A61L 2430/02* (2013.01)

(56) References Cited

U.S. PATENT DOCUMENTS

2010/0121446 A1* 5/2010 Bruce ..................... A61L 27/04 29/428
2010/0215718 A1* 8/2010 Swords ................... A61L 27/56 424/549
2015/0245911 A1* 9/2015 Yang ..................... A61F 2/2846 623/23.5
2016/0184569 A1* 6/2016 Lathuiliere ............. A61F 2/022 604/93.01

* cited by examiner

TITANIUM MESH COVERED WITH BIOCOMPATIBLE POLYPROPYLENE FILM FOR COVERING AND PROTECTING BONE GRAFTS/BIOMATERIALS AND PROCESS FOR OBTAINING SAME

CROSS REFERENCE TO RELATED APPLICATION

This application is for entry into the U.S. National Phase from which priority is claimed under all applicable sections of Title 35 of the United States Code including, but not limited to, Sections 120, 363, and 365(c) to International Application No. PCT/BR2023/050208 filed on Jun. 22, 2023, and which in turn claims priority under 35 USC 119 to Brazilian patent application Ser. No. 1020220131236 filed on Jun. 30, 2022, the contents of which are incorporated by reference herein in its entirety as part of the present application.

TECHNOLOGY SECTOR OF THE INVENTION

The present invention belongs to the biomaterials sector for covering and protecting bone grafts/biomaterials, and it refers, more specifically, to a titanium mesh, covered with a biocompatible polypropylene film, which aims to obtain an increase in bone volume, using biomaterials or using grafts in their most varied forms, such as autogenous bone (bone from the individual), allogenous (bone from individuals of the same species), xenogeneic (bone from individuals from different species) for subsequent accommodation of osteointegrable implants.

STATE OF THE ART

It is well-known that most of the barriers used for guided bone regeneration are made of expanded polytetrafluoroethylene (ePTFE), which has relative permeability, given the existence of porosities on its surface.

Said barriers must be covered by loose connective tissue created by surgical flaps in the area in which a bone defect is to be corrected. So, in this context, the displacement of tissue to cover the barrier causes several inconveniences, as a result of the large quantity required to cover the defect, thus making the surgical procedure difficult, which increases postoperative morbidity.

Another inconvenience is that they are used to obtain guided bone regeneration caused by their low consistency, resulting in the impossibility of keeping the framework required for adequate blood entrapment that leads to the formation and organization of the clot, corresponding to the first phase of bone regeneration. Therefore, barriers of this type do not have a defined morphology and end up collapsing.

In order to prevent the barriers from collapsing and maintaining their shape, it is recommended to fill the defect with bone grafts or bone substitute biomaterials. However, filling materials end up interfering with the physiological process of regeneration, since they need to be reabsorbed to make way for the formation of new bone tissue, something that does not always occur fully or partially. Even though this occurs fully, in the vast majority of cases there is the formation of loose connective tissue in the defect, instead of calcified tissue.

Such problems were solved by BR 202013003809-7, from the same inventor of this patent, which showed a polypropylene barrier, the difference between them being the presence of roughness on both surfaces and that they may or may not receive metallic reinforcement to improve the necessary framework for blood entrapment in intraoral or extraoral guided bone regeneration, whether with or without bone grafts and/or biomaterials. However, advances in technology could be made to solve other technical problems.

It was also noticed that bone defects, especially large ones that require filling, use a reinforcing titanium mesh held in position with the aid of screws attached to the bone tissue, preferably adjacent to the margins of said defects. The function of the titanium mesh is to keep the grafted material in position until the entire reconstructive process is completed. However, the mesh cannot be exposed and must be completely covered with loose connective tissue using surgical flaps, which leads to great postoperative morbidity. Despite solving the structural problem, at the end of the interaction process between the grafted tissue and the pre-existing tissue, the mesh remains wrapped in the regenerated tissue and often cannot be removed, and if it were, it would result in the formation of a new bone defect, jeopardizing the entire repair procedure. Keeping the mesh in place can cause complications in the medium/long term, resulting from late exposure to the oral environment, leading to infections.

INNOVATION OF THE INVENTION

When only titanium mesh is used to provide stability and keep the grafts or biomaterials in the area to be repaired, during the healing period, these materials penetrate through the perforations in these meshes, making it difficult to remove them after they have fulfilled their role. This harms the intended result, as in addition to being very difficult to remove the mesh, part of the material that was used is removed along with the mesh, greatly reducing the amount of material used to increase volume.

However, when using the mesh protected with the polypropylene film of this patent, blocking the perforations, the materials used to increase volume do not penetrate the perforations of the mesh, as they are blocked by the polypropylene film, making these meshes 100% impermeable. This makes it easy to remove the mesh and as there is no penetration of materials into the perforations, the implants are placed in a large quantity of bone tissue obtained.

Another innovation is that the titanium mesh applied with polypropylene film, unlike when it does not have this protection, does not require its total coverage by surgical flaps, facilitating the surgical technique, thus avoiding postoperative complications, due to exposures that often occur from unprotected meshes.

Therefore, with the present invention we obtain the advantage of being able to keep the mesh intentionally exposed to the oral environment, placed on the materials used to achieve an increase in bone volume, regardless of the materials used under it, whether they are grafts or biomaterials (synthetic materials). This fact brings greater comfort to the patient, as it provides a postoperative period with very low morbidity and a quick recovery. Furthermore, the surgical procedure is easier to be performed by the Dental Surgeon, as there is no need for large incisions to detach the soft tissues where the graft will be made, with the purpose of burying the protected mesh, which normally brings a series of postoperative problems, including infections with unpredictable consequences.

DESCRIPTION OF THE ATTACHED DRAWINGS

In order for this invention to be fully understood and put into practice by any technician in this technology segment, it will be described in a clear, concise and sufficient way, based on the attached drawings, which illustrate and support it, listed below:

DETAILED DESCRIPTION OF THE INVENTION

Figure 1:
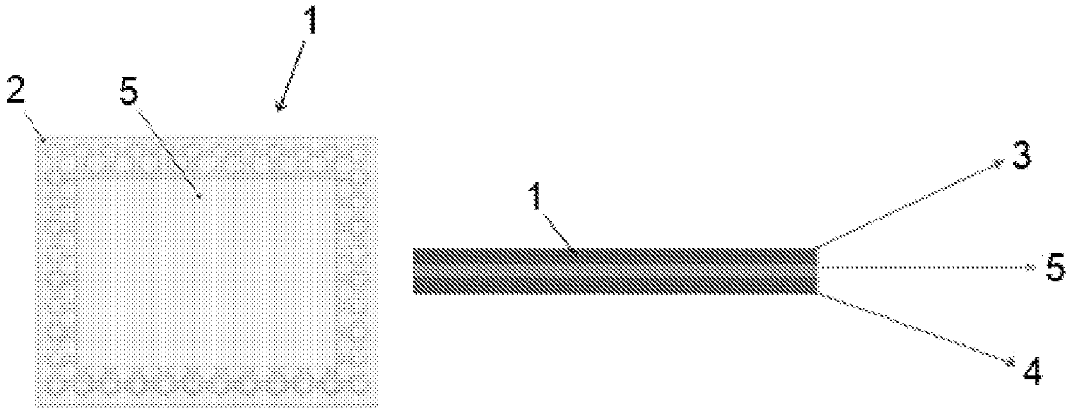
FIG. 1 represents the top and sectional view of the titanium mesh in between the polypropylene film.
Figure 2:
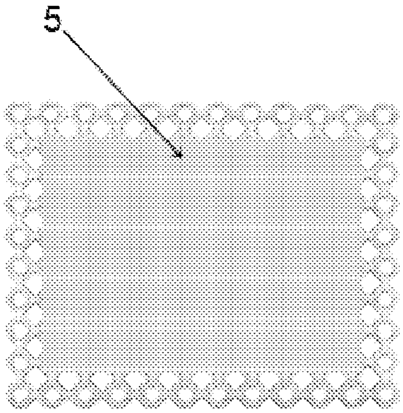
FIG. 2 represents the top view of the perforated titanium mesh.
Figure 3:
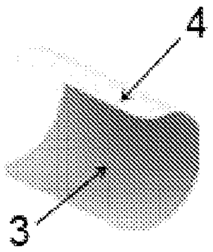
FIG. 3 represents the perspective view of the polypropylene film.

The product (1) is manufactured from a titanium mesh (5) covered by a biocompatible polypropylene film on both sides, consisting of an internal surface (3) and an external surface (4), in such a way that the titanium mesh (5) remains in between the polypropylene films, and may have an edge (2) of at least 1 mm, or not necessarily have said edge (2).

The internal surface (3) has a roughness that can vary from 0.1 to 0.9 μm and the external surface (4) has a similar roughness of 0.1 to 0.9 μm.

The film (2) used is a polypropylene film, which in itself has different roughness, and can be worked on by modifying its internal (3) or external (4) surfaces, keeping the intrinsic roughness of the material or being subjected to some surface treatment in order to increase it. Friction, dry or wet thermal treatments allow the internal surface band (3) and the external surface (4) to achieve roughness of up to 10 μm.

The treatment can only occur on the raw material, that is, on the polypropylene film (2), as can occur on the polypropylene film (2) with the titanium mesh (5).

The manufacturing process occurs through the following steps: a) Two layers of this film cover the titanium mesh (5) on both sides, promoting sealing through the perforations in the mesh, as well as in areas beyond the size of the mesh, that is, free from the mesh, forming a film-film sealing edge (2); b) In the regions of the mesh (5), film-Ti and film-film adhesion occurs, through the perforations in the mesh, which generates double sealing protection, making the mesh remain intact until its complete role is fulfilled; c) The film is overlaid on both sides of the titanium mesh, promoting adhesion by passing through rollers that are heated to 150° C. in a thermo-laminator, thus promoting Ti-film sealing in the region where there is no perforation in the titanium mesh and film-film in the perforated region of the titanium mesh: d) After sealing, the product will exit the machine continuously, then the polypropylene film is cut between one titanium mesh and another, obtaining different products (1).

The polypropylene film itself with the mesh is an innovation, as it is always used without a mesh. The perforations in the mesh (5) are to reduce weight and make it more malleable, in addition to providing a place for fastening screws to pass through when necessary.

More particularly, suitable formats and dimensions can be assumed to meet different treatment needs for guided bone regeneration, being manufactured in biocompatible polypropylene film so that both surfaces (3)(4) can be in contact with the oral environment or in contact with the graft or biomaterials. In other words, there is no concern about which side should be exposed to the oral environment, since taking the standard deviation verified in the roughness tests, both can be considered equal regarding the external or internal side of the film. Although the sides present some degree of difference in roughness.

The product incorporates the metal mesh (5) in between the polypropylene film, with the aim of structuring the product when used in larger bone defects, being able to occupy the entire area or partial areas-when using the mesh, it will be defined by the size of the defect to be regenerated, that is, it can be used by customizing it through cutting to better adapt to the defect. The surface that is exposed to the oral environment makes it difficult for food residue to accumulate, as well as the colonization of microorganisms, protecting the filling material used. Due to the lack of porosity in the film, there is no need to completely cover the mesh. Furthermore, the titanium mesh (5) integrated into the film does not allow the adhesion of soft or calcified tissues, greatly facilitating their removal after cicatrization.

It is important to highlight that the figures and description made do not have the power to limit the ways of implementing the inventive concept proposed herein, but rather to illustrate and make understandable the conceptual innovations revealed in this solution. Therefore, the descriptions and images must be construed in an illustrative and non-limiting way, and there may be other equivalent or analogous ways of implementing the inventive concept revealed herein and which do not deviate from the spectrum of protection outlined in the proposed solution.

What is claimed is:

1. An implantable intraoral mesh sized and configured for covering and protecting bone grafts/biomaterials, the implantable intraoral mesh formed by a titanium mesh covered in its entirety by a pellicle of biocompatible polypropylene film on opposite sides of the titanium mesh, such that the titanium mesh remains in between the polypropylene films, wherein the biocompatible polypropylene film comprises an internal surface having a roughness of 0.1 μm to 0.9 μm, and an external surface having a roughness of 0.1 μm to 0.9 μm, wherein the pellicle of biocompatible polypropylene film extends beyond edges of the titanium mesh to form an edge of the implantable intraoral mesh of at least 1 mm in length.

* * * * *